United States Patent [19]
Robinson

[11] Patent Number: 5,474,768
[45] Date of Patent: Dec. 12, 1995

[54] VAGINAL TISSUE MOISTURIZING COMPOSITION AND METHOD

[76] Inventor: Joseph R. Robinson, 41 Chequamegon Rd., Madison, Wis. 53719

[21] Appl. No.: 15,683

[22] Filed: Feb. 9, 1993

Related U.S. Application Data

[63] Continuation of Ser. No. 732,738, Jul. 18, 1991, abandoned, which is a continuation of Ser. No. 429,755, Oct. 31, 1989, abandoned.

[51] Int. Cl.$^6$ .............................. A61K 9/10; A61K 31/75
[52] U.S. Cl. ................................. 424/78.31; 424/78.02; 424/470; 514/967; 514/969
[58] Field of Search .................... 424/78.1, 78.02, 424/78.31; 514/967, 969

[56] References Cited

U.S. PATENT DOCUMENTS

| | | | |
|---|---|---|---|
| 2,823,163 | 2/1958 | Thoms | 424/78.1 |
| 4,615,697 | 10/1986 | Robinson | 604/890 |
| 4,863,725 | 9/1989 | Deckner | 424/81 |

FOREIGN PATENT DOCUMENTS

| | | |
|---|---|---|
| 674520 | 6/1966 | Belgium . |
| 0050480 | 4/1982 | European Pat. Off. . |
| 2419046 | 10/1975 | Germany . |
| 3400106 | 11/1985 | Germany . |
| 61-72706 | 4/1986 | Japan . |

*Primary Examiner*—Peter F. Kulkosky

[57] ABSTRACT

A composition and method of moisturizing mammalian vaginal membranous tissue is disclosed. The composition utilized in this method includes water, a bioadhesive polymer as the moisturizing agent and a consistency-enhancing agent. The bioadhesive is a water-swellable, but water-insoluble, particulate, fibrous, cross-linked carboxy-functional polymer containing (a) a plurality of repeating units of which at least about 80 percent contain at least one carboxyl functionality, and (b) about 0.05 to about 1.5 percent cross-linking agent substantially free from polyalkenyl polyether. The consistency-enhancing agent is a watersoluble or -dispersible anionic or non-ionic polymer. The composition is contacted with the vaginal mucous membrane to be moisturized, and that contact is maintained for a time period sufficient to moisturize the contacted area.

22 Claims, 3 Drawing Sheets

VAGINAL TISSUE MOISTURIZING COMPOSITION AND METHOD

This application is a continuation of application Ser. No. 07/732,738 filed Jul. 18, 1991 now abandoned, which was a continuation of application Ser. No. 07/429,755, filed on Oct. 31, 1989, now abandoned.

DESCRIPTION

1. Technical Field

This invention contemplates moisturizing of vaginal mucous membranes, and particularly a method and composition for moisturizing that includes water, a particular bioadhesive and a consistency-enhancing agent.

2. Background Art

Several conditions produce drying or desiccation of membranous tissue of the body. These conditions produce dry mouth (xerostomia), dry eye and dry vaginal, dry nasal or dry rectal mucosa, and/or dry skin that are aesthetically unpleasing and/or irritating to the individuals manifesting such conditions.

Methods for moisturization of dry tissue principally utilize creams, lotions, gel or salves that are applied to the affected tissue in an attempt to prevent further dehydration of the tissue by placing a water-impermeable hydrophobic barrier over the treated tissue. Petrolatum, mineral oil, lanolin and isopropyl myristate are exemplary hydrophobic materials so used. These preparations are of limited usefulness over a prolonged period of time.

Hydrophilic small molecules such as glycerin and glycerin/water mixtures, urea, and propylene glycol are known humectants said to be useful in moisturizing skin. Naturally occurring macromolecules such as collagen, hyaluronic acid, elastin and placental proteins have also been used as humectants. Another naturally occurring macromolecule proteolipid obtained from epidermal tissues of several mammals is reported in European Patent Application 86118139.4 (publication No. 0/228/711 A 2, published Jul. 15, 1987), and said to possess humectant properties making it useful in a moisturizer for human skin.

Several synthetic hydrophilic materials, which in the presence of water adhere to the skin and/or mucous membranes, have been used by themselves or in conjunction with one or more active agents to treat various pathological conditions, but not dryness of the skin or mucosa. These hydrophilic materials are often referred to in the art as hydrogels.

Exemplary of such materials are the complex of sulfated sucrose and aluminum hydroxide known generically as sucralfate and available under the trademark CARAFATE® from Marion Laboratories, Inc. of Kansas City, Mo. Sucralfate is used alone or in conjunction with an antacid to treat duodenal ulcers. Another synthetic adherent material, designed for use in the buccal cavity, is a combination of gelatin, pectin and sodium carboxymethylcellulose in a plasticized hydrocarbon gel available under the trademark ORABASE® from Hoyt Laboratories Division of Colgate-Palmolive Co. of Needham, Mass.

A mucosal adherent ointment based upon partly neutralized polymethacrylic acid methyl ester was recently reported by Bremecher et al., *Arzneim. Forsch. Drug Res.*, 33, 591 (1983). That ointment was reported to show a pseudoplastic quality without any thixotropic effect, good mucosal adhesion and no local irritation.

Numerous compositions are known that contain a medicinal component and a polymer carrier. These are generally known as delayed release compositions.

For example, in U.S. Pat. No. 3,074,852, the hydrogel polymer carrier is disclosed as being a polymer of U.S. Pat. No. 2,798,053, prepared by polymerization of polyalkenyl polyether as cross-linking agent with acrylic acid, or its equivalent. The polymerization is reported to be carried out in a hydrocarbon diluent with a free radical catalyst. The cross-linked polymer utilized contains acrylic acid cross-linked with about 0.75 to about 2 percent by weight of the polymer of a copolymerized polyalkenyl polyether. Exemplary polyalkenyl polyethers are disclosed as polyallyl sucrose or polyallyl pentaerythritol that are said to desirably contain an average of at least 3 allyl groups per molecule, the allyl groups being bonded by ether linkages. The exemplary cross-linked polymer is said to be CARBOPOL® 934. The polymer of particular interest in U.S. Pat. No. 3,074,852 is said to be in acid form, and is more particularly described in U.S. Pat. No. 2,909,462, which patent further describes its polymers as being agglomerated by steam action. That particularly described polymer is again reported to be the material sold as CARBOPOL® 934 by B.F. Goodrich Chemical Company.

A neutral hydrogel of a polymer of ethylene glycol methacrylate or similar monomer cross-linked sufficiently to make the polymer insoluble is disclosed in U.S. Pat. No. 3,551,556. Example 8 of that patent also discloses an acid-containing hydrogel prepared by the copolymerization of methacrylic acid and maleic anhydride to form what appears to be a linear, noncross-linked polymer.

U.S. Pat. No. 3,641,237 discloses hydrogels films prepared by polymerization of lower alkoxy lower alkyl acrylates and methacrylates along with a 0–40 percent of a hydrophilic acrylic monomer in the presence of a cross-linking agent. Various monomers are disclosed as useful for the 0–40 percent co-monomers, including hydroxyalkyl acrylates and methacrylates, salts of alpha,beta-unsaturated organic acids and strong acid salts of polymerizable ethylenically unsaturated amine-containing monomers.

European Patent Office Publication No. A1 0 043 319 discloses hydrogel copolymers that contain about 30 to 80 percent acrylate or methacrylate alkyl monoester, about 5 to 68 percent acrylic or methacrylic acid and about 2 to about 15 percent of a bi- or tri-functional acrylate or methacrylate ester. Exemplary bi-functional ester cross-linking agents are ethylene and polyethylene glycol diacrylates. Trimethylolpropane triacrylate and triethylolpropane trimethacrylate are exemplary tri-functional esters.

U.S. Pat. No. 4,226,848 discloses a composition for adhering a pharmaceutical preparation to the mucosa of the oral or nasal cavities. The composition disclosed contains a water-swellable and mucosa-adherent polymeric matrix comprising (a) about 50 to about 95 percent by weight of a cellulose ether and (b) about 50 to about 5 percent by weight of a homo- or copolymer of acrylic acid or a pharmaceutically acceptable salt thereof, with a pharmaceutically effective amount of a medicament dispersed therein.

It is stated in that patent that when either material of the adherent composition is used singly in producing a pharmaceutical preparation, the resulting preparation is unsuitable as a slow-releasing preparation because it does not adhere to the mucosa of the oral or nasal cavity or even when it adheres, it is relatively rapidly disintegrated, dispersed or dissolved by the saliva or other secretions. The specified ratio of the two polymers that form the polymeric matrix is reported to be essentially required in order for the slow-releasing preparation disclosed in that patent not to cause whitening of the mucosa and to release the medicament at a controlled rate. It is further reported that when the polyacrylic acid or salt portion of that composition is present at greater than about 50 percent by weight, the preparation irritates the mucosa, and causes whitening of the mucosa and the marked occurrence of blisters thereon.

The polyacrylic acid or salt portion of the preparation of U.S. Pat. No. 4,226,848 is also described as being water-soluble or water-swellable, but is further described as having a desired, specific range of viscosities at a concentration of 0.2 percent by weight in water. Thus, if that polymer is not truly soluble in water, it is dispersible to at least a sufficient extent to obtain the desired viscosity. An exemplary acrylic acid polymer disclosed therein is the lightly cross-linked acrylic acid/allyl sucrose copolymer available under the trademark CARBOPOL® 934 from B.F. Goodrich Chemical Co., which is said to form a high viscosity gel-like dispersion in water.

U.S. Pat. No. 3,158,538 related to antidiarrheal compositions and their methods of use. The patent discloses use of a composition containing a resin possessing selective intestinal-swellability in conjunction with a tertiary amine anticholinergic agent. The useful resins are said to generally be irregular weight carboxylic type ion-exchange resins loosely cross-linked by means of about 0.2–2.0 weight percent by weight of a polyunsaturated copolymerizable cross-linking agent but which have only a negligible amount of uncross-linked chains present.

One group of polymers said to be useful in No. 3,158,538 are the polycarboxylic acids cross-linked by a polyalkenyl polyether as are disclosed in U.S. Pat. No. 2,798,053. Those are the CARBOPOL® 934-type polymers noted previously.

Another disclosed group of allegedly useful polymers is said to be those disclosed in U.S. Pat. No. 2,810,716. The polymers of that patent are polycarboxylic acids cross-linked by 0.01–2 weight percent of a cross-linker such as a dihydroxydiene or divinyl benzene. The polymers of U.S. Pat. No. 2,810,716 are also described in U.S. Pat. No. 3,202,577 as being useful for diarrhea treatments.

Still another group of polymers disclosed as useful along with the amine-containing cholinergic in U.S. Pat. No. 3,158,538 are the materials described in U.S. Pat. No. 2,923,692. Those polymers are said to be swellable, water-insoluble materials useful as mucilages. They are prepared from a carboxylic acid-containing ethylenic monomer and a cross-linking agent such as divinyl benzene, a diene polymer or polyalkenyl polyethers of polyols. The cross-linker is present at 0.1 to 10.0 percent in those mucilages. The polymers are prepared in a hydrocarbon solvent for the monomers that is a non-solvent for the polymer. After polymerization, the polymer is at least partially neutralized and ground to a size of 100–325 mesh.

Still further, U.S. Pat. No. 3,158,538 teaches that the resin as usually administered consists of hard, sand-like, gritty granules of resin approximately 12 to 14 mesh. The sizes of such mesh are 1.70 millimeters (mm) and 1.40 mm, respectively, according to the Table of Standard Test Sieves (Wire Cloth) found at page F-143 of the *Handbook of Chemistry and Physics*, 54th ed., CRF Press, Cleveland, Ohio (1973).

U.S. Pat. No. 3,390,050 teaches the preparation and use of polycarboxylic acid/medicament-containing beads. Each of the examples that illustrate that invention utilizes a solution of preformed copolymer to which are admixed the medicament and an acrylate or methacrylate monomer or mixture of monomers. The monomer-medicament-copolymer admixture is thereafter emulsified and polymerized to form beads. That patent further teaches that the monomers used are made into a physiologically acceptable polymer of adequate strength that can be at least swollen, e.g., dissolved by the gastric juices.

U.S. Pat. No. 3,121,043 discloses sustained release preparations based upon the interaction of a cross-linked carboxylic acid or anhydride-containing polymer and an amine-containing drug. U.S. Pat. No. 4,192,827 teaches a water-insoluble hydrophilic gel that is used as a carrier for medicaments. The material is prepared from about 30–90 percent of a hydrophilic polymer or copolymer and about 10–70 percent cross-linker that is a terminal diolefinic hydrophobic macromer having a molecular weight of about 400 to about 8000. U.S. Pat. No. 4,450,150 teaches a biodegradable, implantable drug depot and methods of making and using it. The biodegradable polymer portion of the depot is a glutamic acid/ethyl glutamate copolyamide that contains about 5 to about 50 mole percent glutamic acid.

U.S. Pat. No. 4,548,990 discloses a controlled-release drug delivery composition whose cross-linked polymeric portion is prepared from monomers that include 50–99 percent of a water-insoluble monoolefinic monomer or mixture. The polymer is said to swell in ethanol and in water with a swelling ratio of 2:1 to 22:1.

The following teachings relate to body insert structures that are suitable for controlled-release of a medicament.

U.S. Pat. Nos. 3,811,444 and 4,014,987 describe inserts, and specifically ocular inserts. Both require the use of hydrophobic polycarboxylic acids that contain one ionizable carboxylic acid group per 8–22 carbon atoms.

U.S. Pat. No. 4,271,143 teaches an aqueous dispersion of an ophthalmic drug and a high molecular weight polymer. The disclosed polymers are water-soluble or dispersible to an extent that the viscosity of an aqueous composition can be measured. The two polymers mentioned as useful are CARBOPOL® and an ethylene-maleic acid copolymer.

U.S. Pat. No. 4,478,818 teaches an intraocular depot device that provides controlled-release of a steroid, such as fluorometholone, in two different forms. In one embodiment, the polymers said to be useful for encapsulating the depot device are said to be substantially impermeable to the passage of the steroid solute, but are permeable to the passage of biological fluid and water. Imbibed fluid is said to generate osmotic pressure that ruptures the polymer and permits release of the steroid.

In a second embodiment, the paired steroids are housed in a so-called diffusional insert having a size of 115 mm by 0.1–7.5 mm. These inserts are said to be fabricated from a wide range of non-specific polymers said to be insoluble in ocular fluids.

U.S. Pat. No. 4,553,973 discloses a drug-containing walled osmotic device that contains a compartment having a passageway communicating with the exterior of the device. The wall is comprised of a cellulose ether and a permeability enhancer. The semipermeable wall can also contain a water-soluble acrylic acid polymer or a water-insoluble acrylic acid polymer such as CARBOPOL®.

U.S. Pat. No. 4,608,048 discloses a multicompartmented osmotic device for drug delivery. Some embodiments of the disclosed invention include a hydrophilic film-forming material permeable to the passage of external fluid but impermeable to passage of drug. That film is said to be makable from polyacrylic or methacrylic acids or mixtures thereof cross-linked with divinyl benzene.

Still further, U.S. Pat. No. 4,615,697 of the present inventor, inter alia, discloses the use of a polymer that is commercially referred to as polycarbophil as a bioadhesive in the dispensing of a therapeutic agent in controlled release compositions. Another patent of the present inventor, U.S. Pat. No. 4,795,436, discloses the use of such a polymer sized to pass through a 100 mesh sieve screen with fluorometholone.

None of the disclosures of the art discussed before teaches or suggests that polycarbophil or a similar polymer can be used as a moisturizing agent in a composition for dry skin and mucosa as is disclosed hereinafter.

SUMMARY OF THE INVENTION

The present invention contemplates a method of moisturizing vaginal mucosa. In accordance with this method, the vaginal mucosa are contacted with an effective moisturizing amount of an aqueous moisturizing composition that contains water, a moisturizing amount of a bioadhesive polymer and a thickening-smoothing amount of a consistency-enhancing agent. The bioadhesive polymer consists essentially of a bioadhesive, water-swellable, but water-insoluble, particulate, fibrous cross-linked carboxy-functional polymer which is used to contact the skin or mucous membrane of a mammal such as a human. The polymer contains (a) a plurality of repeating units of which at least about 80 percent, and preferably at least about 90 percent, contain at least one carboxyl functionality, and (b) about 0.05 to about 1.5 percent, preferably about 0.1 to about 1.0 percent, cross-linking agent that is substantially free from polyalkenyl polyether, based upon the weights of unpolymerized starting materials; i.e., repeating units and cross-linking agent. The consistency-enhancing agent is a water-dispersible nonionic or anionic polymer. That contact is maintained for a time period sufficient to moisturize the contacted vaginal mucous membrane.

In preferred practice, the dry bioadhesive polymer is sized to pass through a 400 mesh sieve screen, U.S. Standard Sieve Series. It is also preferred that the bioadhesive particle be dispersed in a physiologically tolerable diluent, and particularly a liquid that includes water.

BRIEF DESCRIPTION OF THE DRAWINGS

In the figures forming a part of this disclosure.

Figure 1:
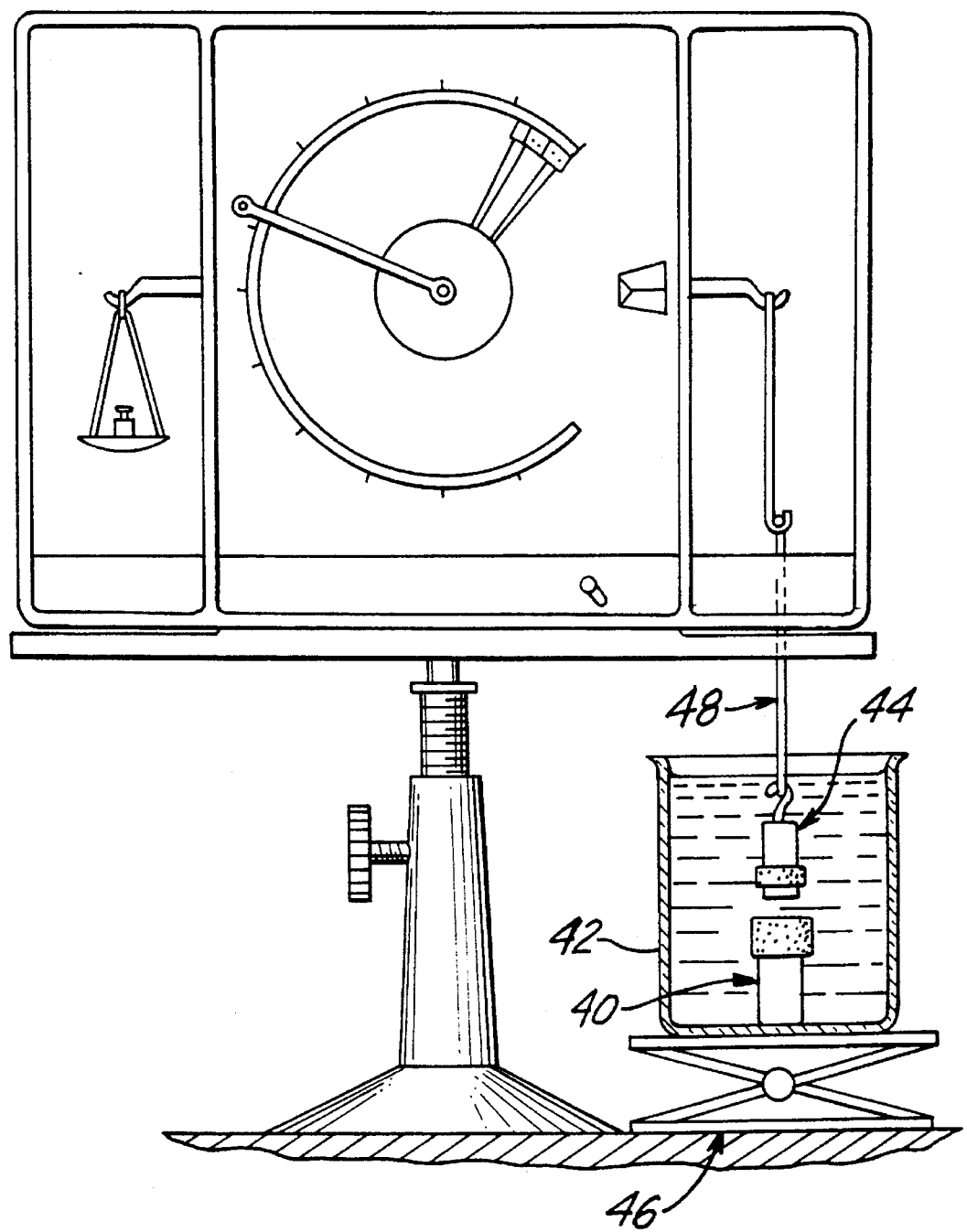
FIG. 1 illustrates a diagrammatic side view of a modified, commercially available surface tensiometer utilized to measure adhesive strength of bioadhesives.

The present invention provides several advantages and benefits.

One advantage of the present invention is that its compositions are not noticeably irritating to the mucosa with which they are contacted.

One of the salient benefits of the present invention is that its moisturizing effects can be relatively long lasting because of insolubility.

Yet another benefit of the present invention is that its compositions can be fabricated with relative ease.

Still further benefits and advantages of the present invention will be apparent to those skilled in the art from the Detailed Description, Examples and claims that follow.

DETAILED DESCRIPTION OF THE INVENTION

The present invention relates to a composition and method of moisturizing the vaginal mucous membrane area by administering that moisturizing composition to a host mammal. The compositions themselves are aqueous compositions that consist essentially of a moisturizing effective amount of a bioadhesive and a water-soluble or water-dispersible, polymeric consistency-enhancing agent.

The moisturizing composition is designed for use on the vaginal mucous membranes (mucosa) of a mammalian animal body, such as that of a human, to which the composition adheres in the presence of a sufficient amount of water to swell the bioadhesive. The composition so adhered to mucosa moisturizes the contacted body area for relatively long periods of time. Such time periods are longer than the time of moisturization for a similar composition that does not include a bioadhesive as disclosed herein. Indeed, for moisturization of mucosa, the bioadhesive moisturizer can remain in place and active for a time period of 10 to about 20 hours; i.e., the turn-over time for mucin or skin.

A composition useful in this invention is substantially non-toxic to the animals in which or on which it is placed. Thus, when contacted with and adhered to vaginal mucosa, a composition causes no apparent whitening or blistering effects due to the bioadhesive, as is reported in U.S. Pat. No. 4,226,848. In addition, adverse immunologic effects from the use of such compositions in and on animals have not been noted.

The method of the present invention utilizes a hydrogel composition that holds substantial quantities of water in contact with the vaginal mucosal area of a host mammal for extended periods of time. This composition functions additionally as a polyelectrolyte and restricts ion efflux from the contacted mucous membrane. Such ion efflux can cause water to move out of tissues. Further, the moisturizing bioadhesive when swollen by an aqueous medium is itself a polyelectrolyte, and produces a Donnan equilibrium effect, resulting in the facilitation of ion influx into the contacted mucosal tissue. This composition is retained in contact with the vaginal mucosal tissue for extended periods of time in the method of the present invention as a result of the substantial bioadhesive, and mucoadhesive, properties of the cross-linked polymer.

The method of moisturizing of the present invention is effective for moisturizing a so-called dry vagina. The art has not recognized a singular objective assay for dry skin or mucous membrane, but certain features are usually noted clinically. One is a lack of pliancy and a flaking that is noted on rubbing. A second is itching and pain of the affected area. A third is a relative lack of plumpness of the affected cells relative to "normal" cells. The cells of such a dry area are typically damaged by usually used cytological or tinctatorial assays.

In accordance with this method of moisturizing, a composition containing water, a moisturizing effective amount of a moisturizing agent and a thickening-smoothing amount of a water-dispersible polymeric consistency-enhancing agent is provided, as described before. An area of vaginal mucous membrane, typically most if not all of the internal vaginal mucosa, to be moisturized is contacted with the provided composition. The external vaginal mucosa and skin can also be contacted. The contact is maintained for a period of time sufficient to moisturize the contacted mucous membrane, and adjoining skin tissues if desired.

Each of the hereinafter-described compositions can be administered in accordance with this method.

A composition useful in this invention can be administered by several means to provide the desired contact between the mucous membrane and the composition. For example, the composition can be applied by rubbing the composition over the area to be moisturized. The composition can be applied by spray, hand, forceps, suppository, plunger, douche or other suitable instrument.

The composition is left in place (contact maintained) for a time sufficient for moisturization of the contacted (treated) area to occur and thereby provide its cosmetic function to the animal. In most circumstances, the administered composition is eliminated from the body by a natural bodily mechanism, such as by dispersion or erosion caused mechanically or by an aqueous body fluid such as vaginal secretions, or by washing.

More specifically, a bioadhesive moisturizing polymer adheres to the mucin that covers the membrane or to the membrane itself. Mucin is replaced (turns over) within about 10 to about 20 hours, usually about every 17 hours, and the adhered bioadhesive moisturizing polymer is lost with the mucin. The bioadhesive moisturizing polymer and consistency-enhancing agent can also be lost by mechanical action at the site of contact, as well as by washing or douching.

The principal moisturizing ingredient of a composition of this invention is a bioadhesive polymer. The active moisturizer consists essentially of the bioadhesive polymer, by which it is meant that although ingredients such as water, the water-dispersible consistency-enhancing agent and adjuvants or diluents can be present, other ingredients that materially alter the basic and novel characteristics of the bioadhesive polymer or a before-described moisturizing composition are absent.

Exemplary of such other ingredients that are absent from the present compositions are the treating agents that are disclosed in U.S. Pat. Nos. 4,615,697 and 4,795,436, which include medicinal agents and cosmetic agents. Thus, a moisturizing composition is free of treating agents, whether those agents are medicinal as is the case for drugs such as hormones, antidiarrheal agents and the like, or cosmetic such as sun screens, vitamins or minerals, keratolytic agents and the like.

This bioadhesive polymer comprises a water-swellable, but water-insoluble, particulate, fibrous, cross-linked carboxy-functional polymer. The polymer contains (a) a plurality of repeating units of which at least about 80 percent contain at least one carboxyl functionality and (b) about 0.05 to about 1.5 percent cross-linking agent substantially free from polyalkenyl polyether, with the percentages being based upon the weights of unpolymerized repeating unit and cross-linking agent, respectively. In more preferred practice, at least about 90 percent of the repeating units contain at least one carboxyl functionality, and in still more preferred practice, at least 95 percent of those repeating units contain at least one carboxyl functionality. Most preferably, the bioadhesive is a reaction product of the polymerization of only a single carboxyl-functional monomer and the cross-linking agent. Also in more preferred practice, the bioadhesive contains about 0.1 to about 1 percent by weight of polymerized cross-linking agent.

A bioadhesive can be broadly defined as a material that adheres to a live or freshly killed biological surface such as mucous membrane or skin tissue. Bioadhesion, as that phrase is used herein to define a useful bioadhesive moisturizing polymer, is assayed by a procedure described hereinafter in Example 2 that measures the force required to separate two layers of freshly excised rabbit stomach tissue that are adhered together by an adhesive. Using this procedure, a bioadhesive can be defined as a material that requires a force of at least about 50 dynes/cm$^2$ to separate two adhered, freshly excised pieces of rabbit stomach tissue, following the procedure of Example 2. Upper limits for forces required to separate the freshly excised rabbit tissue are presently unknown, but are believed to be at least about 2000 dynes/cm$^2$.

For purposes of comparison, a non-bioadhesive, cross-linked, strongly acidic macromolecular and swellable polymer having sulfonic acid functionality such as the cation exchange resin sold by Rohm and Haas, Company of Philadelphia, Pa. as its AMBERLITE® 200 exchange resin requires almost no force to separate the excised tissue, while homopoly(2-hydroxyethyl methacrylate) (p-HEMA) requires a force of about 29 dynes/cm$^2$ for separation.

As noted previously, at least about 80 percent of the repeating units of the bioadhesive contain at least one carboxyl functionality. Exemplary monomers that provide these repeating units are monoethylenically unsaturated and include acrylic acid, methacrylic acid, fumaric acid, maleic acid, maleic anhydride which may be hydrolyzed into its acid form during or after polymerization, itaconic acid, crotonic acid, and the like. Each of these acids can be used alone or in combination with other such acids or with one or more pharmaceutically or cosmetically acceptable salts of those acids. Acrylic acid is a particularly preferred monomer for providing the carboxyl group-containing repeating units of the bioadhesive polymer.

The bioadhesive polymers useful in this invention are cross-linked by cross-linking agents as are known in the art. The cross-linking agent is substantially free from polyalkenyl polyethers, and is particularly free from polyalkenyl polyethers such as polyallyl sucrose or polyallyl pentaerythritol containing an average of at least three allyl groups per molecule as are reportedly present in CARBOPOL® 934. Exemplary of useful cross-linking agents are divinylbenzene, N,N-diallylacrylamide, 3, 4-dihydroxy-1,5-hexadiene, 2,5-dimethyl-1,5-hexadiene and the like.

The amount of cross-linking of the bioadhesive is of some import. When less than about 0.05 weight percent of an appropriate cross-linking agent is present, the bioadhesive tends to become water-soluble, or water-dispersible, thereby losing its desired water-insoluble, water-swellable, fibrous character that is important to the invention. When greater than about 1 percent cross-linking agent is present, the water-swellability of the bioadhesive begins to decrease appreciably. At cross-linking agent levels greater than about 1.5 percent, the water-swellability is sufficiently decreased so as to make the bioadhesive lose its desired, functional characteristics. Preferably, the cross-linking agent is present at about 0.1 to about 1 percent.

The above amounts of carboxy-functional repeating units and cross-linking agent are used to define the bioadhesive, but specifically refer to the percentages of those predecessor, unpolymerized monomers in the reaction mixture from which the bioadhesive is polymerized. These pre-polymerization amounts are utilized because of the great difficulty in analyzing the polymerized bioadhesive. Although the amounts refer to the pre-polymerized monomers, it is believed that the bioadhesives contain substantially similar amounts of those monomers in polymerized form.

A bioadhesive polymer useful herein can thus be in part defined as a reaction product of the copolymerization of at least 80 weight percent monoethylenically unsaturated carboxy-functional monomer and about 0.05 to about 1.5 weight percent of a cross-linking agent free of polyalkenyl polyether. The remaining monomers that can be present to constitute 100 percent by weight of the monomers are discussed below.

In addition to the above two ingredients, the bioadhesive polymer can also include polymerized monoethylenically unsaturated repeating units such as $C_1$–$C_6$ alkyl esters of one or more of the above-described acids such as hexyl acrylate, butyl methacrylate and methyl crotonate; hydroxyalkylene-functional esters of the above-described acids that contain a per molecule average of 1 to about 4 oxyalkylene groups containing 2–3 carbon atoms such as hydroxyethyl methacrylate, hydroxypropyl acrylate and tetraethylene glycol monoacrylate; methacrylamide, acrylamide and their $C_1$–$C_4$ mono- and di-alkyl derivatives such as N-methyl acrylamide, N-butyl methacrylamide and N,N-dimethyl acrylamide; styrene; and the like as are known in the art as being copolymerizable with the above described carboxyl functionality-containing monomers and cross-linking agents. The bioadhesive polymers most preferably are prepared from only the monoethylenically unsaturated carboxy-functional monomer and the cross-linking agent.

A bioadhesive moisturizing polymer useful herein can be prepared by conventional free radical polymerization techniques utilizing initiators such as benzoyl peroxide, azobisisobutyronitrile, and the like, is polymerized in an aqueous medium, and is not agglomerated by steam action. Exemplary preparations of useful bioadhesives are provided hereinafter and can also be found in U.S. Pat. Nos. 2,810,716 and 3,202,577, whose disclosures are incorporated herein by reference.

The polymers described in U.S. Pat. No. 3,202,577 are reported therein to be useful in treating diarrheal states. The disclosures of that patent are directed to the use of its polymers as bulking or dehydrating agents, and not as bioadhesives.

A polymer similar to those of U.S. Pat. No. 2,810,716 or No. 3,202,577 is used in commercial form as a calcium salt and is available generically as calcium polycarbophil in chewable tablet form. Such a polymer appears to be produced in accordance with U.S. Pat. No. 3,297,664 and is not contemplated herein.

The bioadhesive useful herein is fibrous or particulate, and swellable in water, but is insoluble in water. Thus, the bioadhesive useful herein can be distinguished from those polymers of U.S. Pat. Nos. 3,074,852, 3,330,729 and 4,226,848, described hereinbefore that utilize CARBOPOL® 934. That polymer does provide adhesion as discussed herein, but is water-soluble, making it less desirable, and is therefore excluded from the bioadhesives of this invention. Thus, CARBOPOL® 934 is said in U.S. Pat. No. 4,226,848 to be sufficiently water-soluble to provide a measurable viscosity at a concentration of 0.2 percent by weight in water. Contrarily, as illustrated hereinafter in the examples, the bioadhesives useful herein are prepared in aqueous solution and separate therefrom after polymerization.

In addition, the polymers of U.S. Pat. Nos. 3,074,852, 3,330,729 and 4,226,848 are cross-linked by a polyalkenyl polyether such as the triallyl ether of sucrose or the triallyl ether of pentaerythritol. The bioadhesives of the present invention are substantially free of such cross-links, particularly of cross-links by agents having an average of at least about three allyl groups per molecule.

Nevertheless, the fibrous, bioadhesive polymers of this invention are swellable in water; i.e., the polymer particles sorb water (adsorb or absorb) and thereby become larger in size in the presence of water. The water used for that swelling, is typically that provided by the aqueous composition of the present invention or it can in part be that provided by the body of the treated animal, such as by moisture transpiration or secretion through the mucosa or by vaginal mucosal secretions themselves, although the latter are normally not present or are present in relatively small amounts that give rise to the need for the composition.

The size of the bioadhesive particles has an effect upon the compositions of this invention. It is apparent that the bioadhesive particles should not be so large that the composition cannot be administered without undue difficulty. Similarly, particles sized larger than those discussed below can sometimes cause pain and irritation when administered. In addition, it appears as though particles sized as discussed below provide improved function to the moisturizer composition as compared to particles that are larger in size; i.e., in the longest dimension.

Typically, at the maximum, a useful bioadhesive polymer is sized to pass through a sieve screen having a 400 mesh (U.S. Standard Sieve Series); i.e., a 38 micron opening. Preferably, the bioadhesive polymer particles are smaller still and are sized so that the longest dimension is about 20 microns. Most preferably, the particles have a number average size of about 2 microns to about 5 microns in the longest dimension. Particles of a desired size can be obtained, for example, by grinding, crushing or otherwise comminuting larger particles, as well as by direct polymerization.

Particles having a relatively small size have a greater surface area per unit weight, swell more rapidly, and appear to adhere better than do particles having a relatively large size, and thus, a relatively small size is preferred for the particles. Bioadhesion measurements discussed before and in Example 2 hereinafter are carried out for convenience using a bioadhesive sized to pass through a 30 mesh sieve screen and be retained on a 40 mesh sieve screen (U.S. Standard Sieve Series); i.e., 30/40 mesh size.

Bioadhesion has not been found to be a function of the molecular weight of the bioadhesive. Consequently, the bioadhesive can be of substantially any molecular weight, so long as its adhesion in the adhesion test described hereinafter is at least about 50 dynes/cm$^2$.

As noted previously, the bioadhesives are polymerized in an aqueous medium. In preferred practice that aqueous medium is a saturated solution of an alkaline earth metal salt such as magnesium sulfate. The alkaline earth metal salt serves at least two functions. First, it increases the density of the polymerization medium so that the polymerized bioadhesive floats on the surface of the aqueous medium and can be easily removed therefrom. Second, the use of magnesium sulfate, in particular, reduces the swelling of the bioadhesive in the aqueous medium so that polymerization and recovery are facilitated. Bioadhesives so prepared typically contain about 0.5 to about 1 percent of the alkaline earth metal ion after several water rinsings of the polymer. These polymers thus differ from those in which an alkaline earth metal hydroxide is used to neutralize the carboxyl groups as in calcium or magnesium polycarbophil.

Particularly preferred bioadhesives that are commercially available are those materials sold under the designation polycarbophil by A. H. Robins Co. of Richmond, Va. and "EX55" by B.F. Goodrich Chemical Co. of Cleveland, Ohio, the manufacturer of CARBOPOL® 934 that is also discussed herein. *The United States Pharmacopeia* (U.S.P.) 1980 ed., United States Pharmacopeial Convention, Inc., Rockville, Md., at page 638, indicates that polycarbophil is a polyacrylic acid cross-linked with divinyl glycol that has a residue on ignition of less than 4.0 percent and absorbs about 60 times its original weight in test B under Absorbing Power. The 1985 edition of the U.S.P. lists only calcium polycarbophil that contains 18–22 percent calcium and is different from the material described in the 1980 edition.

The material designated as "EX55" from the B. F. Goodrich Co., above, sorbs (absorbs and adsorbs) about 40 to about 60 times its weight of water. That sorption value is similar to the sorption capacity of natural mucin. A useful bioadhesive is also a polyanionic polymer with a charge density similar to mucin.

Useful bioadhesive polymers of this invention were examined as to their densities, which are typically about 1.30–1.70 grams/cubic centimeter (g/cc). The cross-linking percentage was found to have a small effect upon the resulting density of illustrative, synthesized polymers as is shown in the Table below. Also shown in that Table is a somewhat greater effect upon density than is observed for different starting monomers.

| Densities of Useful Bioadhesives | | | |
|---|---|---|---|
| Bioadhesive | | | Density[2] |
| Monomer | Cross-linker | %-CL[1] | (g/cc[3]) |
| acrylic acid | 3,4-dihydroxy-1,5-hexadiene | 0.05 | 1.49 |
| acrylic acid | 3,4-dihydroxy-1,5-hexadiene | 0.30 | 1.56 |
| acrylic acid | 3,4-dihydroxy-1,5-hexadiene | 0.60 | 1.57 |
| acrylic acid | 3,4-dihydroxy-1,5-hexadiene | 1.20 | 1.62 |
| acrylic acid | 3,4-dihydroxy-1,5-hexadiene | 2.00 | 1.65 |
| methacrylic acid | 2,5-dimethyl-1,5-hexadiene | 0.30 | 1.47 |
| methacrylic acid | divinyl benzene | 0.30 | 1.36 |

[1]%-CL = weight percent cross-linking agent based upon total polymerizable monomers.
[2]Density of each polymer was determined in a 2 milliliter specific gravity bottle at 25 C. Benzene of known density (0.874 g/cc) was used at the medium.
[3]g/cc = grams per cubic centimeter.

The bioadhesive moisturizing agent is present in the compositions of this invention in an amount that is sufficient to provide moisturization for a desired period of time for which the composition of this invention is to be administered, and such an amount is referred to herein as "an effective moisturizing amount". As is well known, effective amounts of agents vary with the particular agent employed, the condition being treated and the rate at which the composition containing the agent is eliminated from the body, as well as varying with the animal in which it is used. Consequently, effective amounts of moisturizing agents cannot be defined for each agent. Thus, an effective moisturizing amount is that amount, which in a composition of this invention, provides a sufficient amount of the moisturizing agent to provide the requisite moisturization on the body of the treated animal for the desired period of time. An effective amount can therefore also be defined as a moisturizing amount.

As there is no universally accepted assay for dry skin or mucosa, there also is no universally accepted assay for moisturized skin or mucosa. Both conditions are usually determined subjectively by the person who has dry or moisturized skin or mucosa and by clinicians skilled in making such evaluations.

Nevertheless, some criteria for moisturized skin and mucosa include a pliant, non-flaky surface, an absence of itching, and a relative plumpness of the cells of the treated area. Relative plumpness can be examined by scanning electron microscopy of casts made from the treated areas.

Several workers have tried to quantify dry and moisturized skin by various techniques. For example, Leveque et al., *J. Soc. Cosmet. Chem.*, 34:419–420 (Dec. 1983) have reviewed in vivo impedance methods for such assays. Potts, *J. Soc. Cosmet. Chem.*, 37:9–33 (Jan./Feb. 1986) reviewed several techniques for both in vivo and vitro measurements of stratum corneum hydration. Lieb et al., *J. Soc. Cosmet. Chem.*, 30:107–119 (March/April 1988) discuss an in vitro method for measuring transepidermal water loss (TEWL). In the latter paper, oleaginous materials such as mineral oil that form an occlusive layer over the skin tend to lower TEWL, whereas humectant materials such as glycerin in water raised the TEWL values.

Although none of the methods discussed in any of the above papers is universally accepted or applicable, a TEWL method such as that described by Lieb et al. for humectant-type materials appears to be useful for the bioadhesive moisturizing polymers herein when quantitative data are required. Otherwise, the expertise of trained observers and/or comments of clinical subjects are sufficient assays for a useful moisturizing method as discussed herein.

A moisturizing composition utilized in the method of the present invention is designed to provide about 0.25 grams to about 15 grams (g) of bioadhesive per 100 milliliters (about 0.25 to about 15 weight percent) of the composition. More preferably, a bioadhesive polymer is present at about 2 to about 5 grams per 100 grams of composition (about 2 to about 5 weight percent).

In addition to water and the before-mentioned bioadhesive polymer, a composition of the present invention contains a thickening-smoothing amount of a consistency-enhancing agent that is a water-soluble or water-dispersible polymer. Specific consistency adjusting agents are discussed hereinafter.

A before-discussed bioadhesive polymer swells in water, but neither dissolves nor disperses as does a consistency-enhancing agent. Such a polymer is thus said to be water-insoluble, but can and does affect viscosity, albeit poorly and with little control.

A consistency-enhancing agent useful herein possesses sufficient water-solubility or -dispersibility that even small amounts can radically alter the viscosity of an aqueous composition. Such materials can exhibit bioadhesion, but because of their solubility or dispersibility in aqueous media, they tend to be lost relative quickly from a composition and thereby do not provide the relatively long term moisturization that is provided by a before-discussed bioadhesive polymer.

For ease of expression, a consistency-enhancing agent will generally be referred to herein as being water-dispersible. This is particularly apt inasmuch as a solution can be viewed as the ultimate dispersion.

Regardless of whether a consistency-enhancing agent is dispersed or truly dissolved, a composition of such an agent present at up to about 10 percent in deionized or distilled water forms a single phase to the naked eye at 20 degrees C., and once prepared does not exhibit separation when maintained at 20 degrees C. for 24 hours. Where the consistency-adjusting agent is an acid, cations such as sodium, potassium and ammonium ions that are utilized to disperse or dissolve the consistency-adjusting agent can also be present in the composition.

Exemplary consistency-enhancing agents include anionic (carboxyl group-containing) and non-ionic polymers such as those containing a plurality of carboxyl groups and those containing a plurality of $C_2$–$C_3$ hydroxyalkyl groups. Specific, preferred consistency-enhancing polymer agents include carboxymethyl cellulose, hydroxypropyl cellulose, hydroxyethyl starch derivatives, hydroxyethyl cellulose, gums such as tragacanth, hydroxyethylacrylate or methacrylate, polyacrylamide, and lightly cross-linked polyacrylic acid polymers like the before-described CARBOPOL® 934, which is particularly preferred. CARBOPOL® 934 is reportedly a polymer of acrylic acid that is cross-linked with a polyallyl sucrose (a polyalkenyl sucrose) containing an average of at least three allyl groups per molecule. The preferred consistency-enhancing agent polymers are thus seen to be derivatized polysaccharides and polyacrylic acids; i.e., amides and hydroxyethyl esters. Additional consistency-enhancing polymer agents include polyvinyl pyrrolidone, polyvinyl alcohol and polyethylene oxide.

A consistency-enhancing agent functions in a composition described herein as its name implies; i.e., to enhance the consistency of the composition. That enhancement is in two areas: viscosity and texture.

As already noted, a consistency-enhancing agent useful herein is water-dispersible and a relatively small amount of such a material can greatly increase the viscosity of or thicken an aqueous composition. Inasmuch as the bioadhesive lends relatively poorly controlled viscosity-building effects to an aqueous composition, a composition containing only a bioadhesive moisturizing polymeric agent can be too thin and runny or too stiff for a particular purpose such as in a vaginal product.

When admixed in the amounts and under the conditions discussed hereinafter, a bioadhesive moisturizing polymer and a consistency-enhancing polymer combine to provide an appropriately thickened aqueous moisturizing composition. It is not presently known whether the thickening effect observed is due to an additive effect of both materials or to an interaction between the two components since the resulting aqueous compositions behave as non-Newtonian fluids.

A particularly unexpected effect of the admixture of a useful bioadhesive moisturizing polymer and a consistency-enhancing polymer agent is that the texture of the resulting thickened composition is made smoother than when a bioadhesive Doisturizing polymer is utilized alone. Thus, an aqueous composition that contains only a bioadhesive moisturizing polymer can exhibit a stiff and almost gritty feel, and as such could be uncomfortable in a vaginal product particularly during intercourse.

On the other hand, the presence of a consistency-enhancing polymer agent unexpectedly smoothens the aqueous composition so that it exhibits substantially no stiffness or grittiness. That smoothening of texture also provides enhanced lubricity to the composition.

The use of a single amount of the consistency-enhancing polymer agent provides both the required thickening and smoothing. Thus, the amount of that material utilized is described as a thickening-smoothing amount. Although a single amount of that agent is utilized, the consistency-enhancing agent can be a mixture of polymers such as those discussed before.

The consistency-enhancing polymer agent is present in a thickening-smoothing amount, which, along with the other components that can be present in an aqueous composition preferably provides a gel-like consistency with a viscosity of the product of about 4,000 to about 40,000 cps at 25 degrees C., measured as discussed in Example 6. As is discussed in greater detail hereinafter, the viscosity of the composition is a function of several variables, each of which can be changed to alter or maintain a desired viscosity.

A typical composition can contain about 0.25 to about 10 weight percent of a consistency-enhancing agent polymer. More particularly, an amount of about 0.5 weight percent to about 5 weight percent is utilized.

A greater amount of a consistency-enhancing agent is generally utilized with a smaller amount of bioadhesive polymer, and vice versa. For example, a composition at a pH value of 2.2–2.5 containing 0.25 weight percent polycarbophil as the bioadhesive requires about 8–10 weight percent CARBOPOL® 934 to achieve a viscosity appropriate for mechanical placement in the vagina.

The moisturizing water can be provided by the composition or by the contacted mucosa, or both, although typically, the water is provided by the composition. Thus, the bioadhesive moisturizing and consistency-enhancing agents can be admixed and preswollen in an aqueous medium prior to application, or can be applied admixed in an aqueous vehicle that contains enough water to partially hydrate the bioadhesive moisturizing agent particles and the consistency-enhancing agent.

A useful aqueous composition can have a room temperature-consistency of a barely pourable liquid to a gel, the latter being preferred, with the consistency being a function of relative amounts of water, bioadhesive moisturizing polymer, consistency-enhancing polymer agent, osmoticity and the pH value of the composition formed. A relatively low amount of the two polymers in a given amount of water produces a relatively thinner composition than does a greater amount of the polymers, with the pH value being held constant at both concentrations.

The pK of a useful bioadhesive moisturizing polymer is about 3. As a consequence, where a composition is at a pH value of about 5 or greater, substantially all of the acidic protons are neutralized and the polymer-containing composition exhibits its thickest consistency for that concentration. On the other hand, at pH values such as 2, below the polymer's pK value, the composition is relatively thinner, for a given concentration.

The $pk_a$ values for the carboxylic acid-containing consistency-enhancing agents such as the particularly preferred CARBOPOL® 934 are similar to that of a bioadhesive polymer. As a consequence, use of a composition at a pH value of about 5 or greater provides the thickest composition, whereas use of a pH value of about 2 provides the thinnest composition, for a given concentration of consistency-enhancing agent and all other components being held constant. Non-ionic consistency-enhancing agents change their viscosity and that of the composition less over a range of pH values than do anionic materials.

In addition, osmoticity of a composition can also play a role in the viscosity of the composition. Typically, higher solute concentrations decrease the viscosity of a composition when the amounts of bioadhesive polymer, consistency-enhancing polymer, water and the pH value are kept constant. Thus, the viscosity of a before-discussed composition having a pH value in excess of 5 can be reduced from that of a ringing gel to a pourable liquid by increasing the osmoticity of the composition.

An isotonic product has an osmoticity of about 280 to about 320 mOsM, and such an osmoticity is useful herein. The osmoticity of a moisturizing composition can be as high as about 450 to about 500 mOsM.

Pharmaceutically acceptable electrolytes and nonelectrolytes (collectively referred to as solutes) are used for adjusting osmoticity and viscosity of a useful composition. Exemplary pharmaceutically acceptable electrolytes include sodium chloride, potassium chloride, sodium phosphate, potassium phosphate, sodium and potassium sulfates, and sodium and potassium bicarbonates. Exemplary pharmaceutically acceptable non-electrolytes include glycerin, sugars such as glucose and sucrose, sorbitol and urea. Thus, those solutes that are well known for adjusting osmolarity or osmolality are useful herein.

Osmoticity of a given composition is a measured value that is obtained using a vapor phase osmometer.

Thus, a composition containing a bioadhesive moisturizing polymer and carboxy group-containing consistency-enhancing polymer agent at or near the high end of the before-discussed concentrations and at a pH value of about 5 or greater exhibits more gel-like properties. Such compositions can, nevertheless, be extruded in the form of drops from an eye dropper, particularly where sufficient electrolyte or other solute is present to raise the osmoticity to near about 450 mOsM. Conversely, a composition at or near the low end of the before-discussed concentrations and at a pH value below about 3 typically behaves as a barely pourable liquid.

With these extremes of consistency in mind, a skilled worker can readily formulate a moisturizing composition having a desired consistency. It should also be understood that the pH value of a moisturizing composition can change once the composition is contacted with the vaginal mucosa as a result of the local pH value of the area to which the composition is applied.

The moisturizing composition is applied to the vaginal mucosa in an amount sufficient to form a layer of hydrated bioadhesive particles that is substantially continuous over the applied surface. Typically, that layer is several particles thick. In terms of the dry bioadhesive moisturizing agent, the bioadhesive moisturizing agent is applied in an amount of about 1 to about 50 milligrams (mg) per square centimer ($cm^2$) of contacted vaginal mucosa. Application to the vaginal mucosa can be and preferably is in excess of that needed to provide moisturization.

It is, however, more convenient to refer to the amount of bioadhesive moisturizing polymer applied in terms of the total weight of the polymer applied. Thus, the amount of composition is about 1 to about 5 grams of a composition containing about 0.25 to about 3 weight percent of the bioadhesive polymer. This latter amount is in excess of that needed for moisturization, but the excess is useful in providing lubrication during sexual intercourse.

In addition to the bioadhesive polymer moisturizing agent and consistency-enhancing agent, a composition useful in this invention can also contain one or more pharmaceutically or cosmetically acceptable additives that are referred to herein as adjuvants that assist in providing shelf life and customer acceptance of a moisturizing product. Exemplary adjuvants include preservatives, emollients, lubricating oils, emulsifying agents, humectants, coloring agents, and odor providing agents (odorants).

The phrases such as "pharmaceutically acceptable", "cosmetically acceptable" or "physiologically tolerable" are used herein to mean that the material so described can be used for treatments in or on humans or other mammals without causing ill effects, such as toxicity, blistering or whitening of mucosa or skin tissues, and that those materials are not themselves bioadhesive moisturizing agents, as those words are used herein. Exemplary adjuvants can be found in Chapter 67 of *Remington's Pharmaceutical Science*, 16th ed., Osol et al. eds, Mack Publishing Company, Easton, Pa. (1980).

It is noted that the above-mentioned adjuvants can be present in an amount that is greater than the bioadhesive polymer. Even though such can be the case, the adjuvants do not provide the moisturization of the composition, but rather provide emulsification or lubricity or the like, and typically assist in application of the compositions. This is the case where a compound such as glycerin or sorbitol that is a known humectant is present since such materials are water-soluble, non-bioadhesives that are typically lost with perspiration or the like. Lubricating oils and emulsifying agents provide lubricity to a composition for sexual intercourse.

The word "dry" is used herein in relation to a bioadhesive moisturizing polymer to mean that the polymer does not adhere when touched with a finger within a rubber glove, and is substantially unswollen.

A gel-like consistency is preferred for a vaginal moisturizer, with the composition being applied by means of a plunger-type applicator as is well known for use in applying vaginal products.

BEST MODES FOR CARRYING OUT THE INVENTION

EXAMPLE 1

Bioadhesive Polymer Preparation

Bioadhesive polymers useful herein were prepared following the general synthetic procedure discussed immediately below. Specific bioadhesive polymers made in accordance with the general procedure are illustrated in Table 1, hereinafter.

A solution containing 100 milliliters of distilled water and 800 grams of magnesium sulfate ($MgSO_4$–$7H_2O$) was heated to reflux with agitation. A mixture of 1 gram of initiator dissolved in 100 grams of monomeric carboxy-functional repeating unit and the amount of cross-linking agent shown in Table 1 was added to the refluxing aqueous solution with continued stirring. The polymerizing composition so prepared was agitated and heated to the temperature shown in Table 1 for the period of initial polymerization and of post-polymerization curing.

At the termination of the curing time, the polymerized composition was diluted with 150 milliliters of distilled water heated to a temperature of about 95 C. and then strained through a stainless steel sieve having a 40 mesh screen (U.S. Standard Sieve Series). The strained bioadhesive remaining on the screen was washed with one 1 liter portion of water heated to a temperature of about 80 C. followed by five separate 1 liter washings using tepid water. The washed bioadhesive so prepared was then dried in a forced air oven at a temperature of 90 C. for a period of 48 hours.

The bioadhesives so prepared were then used as such or comminuted and sieved to provide a desired particle size.

TABLE 1

| | Bioadhesives | | | | | | |
|---|---|---|---|---|---|---|---|
| Carboxy- | Cross | | Polymerization Conditions | | | | |
| functional Repeating Unit[1] | Linking Agent[2] | Initiator[3] | Poly. Time[4] | T.[5] | Time[6] | Yield[7] | |
| (A) | (a) 0.2 | (1) | 15 | 95 | 2 | 83 | |
| (A) | (b) 1.0 | (1) | 25 | 95 | 18 | 67 | |
| (B) | (a) 1.0 | (1) | 30 | 95 | 48 | 53 | |
| (B) | (b) 1.0 | (1) | 30 | 95 | 48 | 87 | |
| (C)[8] | (a) 1.0 | (1) | — | 65 | 24 | 11 | |
| (D)[8] | (a) 0.2 | (2) | 20 | 95 | 72 | 10 | |
| (A) | (c) 0.2 | (1) | 10 | 95 | 4 | 98 | |
| (B) | (c) 0.2 | (1) | 10 | 95 | 20 | 93 | |

[1] 100 Grams of each of the following carboxy-functional repeating units was used: (A) = acrylic acid; (B) = methacrylic acid; (C) = itaconic acid; and (D) = maleic anhydride.
[2] The numerals of the Table indicate the number of grams of the particular cross-linking agent used. The particular cross-linking agents were: (a) = 3,4-dihydroxy-1,5-hexadiene; (b) = divinyl benzene; and (c) = 2,5-dimethyl-1,5-hexadiene
[3] One gram of the following initiators was used: (1) = benzoyl peroxide; and (2) = azobisisobutyronitrile.
[4] Initial polymerization time in minutes.
[5] Temperature in degrees C. for initial polymerization and post-polymerization cure.
[6] Post-polymerization cure time in hours.
[7] Yield of dried bioadhesive based upon the weights of starting materials and recovered bioadhesive.
[8] A nitrogen sparge was used during polymerization as was deaerated distilled water prepared by boiling distilled water for a period of 10 minutes.

Although optimization of polymerization conditions is not reflected in the data of Table 1, it can be seen from those data that the bioadhesives useful herein are easily prepared in useful quantities. It is noted that the first bioadhesive listed in Table 1 has bioadhesion and other physical and chemical properties that are substantially identical to the commercially available bioadhesive sold under the designation polycarbophil by A.H. Robins Co. of Richmond, Va. as well as that sold under the designation EX55 by B.F. Goodrich Chemical Co. of Cleveland, Ohio.

EXAMPLE 2

Measurement of Adhesion

As noted previously, a bioadhesive moisturizing polymer of this invention is a water-insoluble, but water-swellable, particulate, fibrous, cross-linked carboxy-functional polymer that contains specified amounts of carboxyl functionality and cross-linking agent. In addition, to that chemical definition, a useful bioadhesive by definition must also exhibit an adhesion between two pieces of freshly excised rabbit stomach tissue of at least about 50 dynes/cm$^2$ when measured under specified conditions. Those conditions and the apparatus utilized for that measurement are described hereinbelow.

The apparatus utilized for these measurements is illustrated in FIG. 1. Basically, the apparatus is a standard, surface tensiometer as is available from Biolar Corporation, of North Grafton, Mass. that has been modified by removal of the du Nuoy loop and its replacement by an elongated linking arm 48 and an excised stomach tissue holding means 44.

Fresh stomach was obtained from rabbits and was carefully washed with a chilled solution containing 0.9 weight percent sodium chloride in distilled water (normal saline solution) to remove the contents. The stomach was placed in an aerated, chilled normal saline solution until used.

The tissue was cut into a round shape from the fundus part of the stomach and secured mucosal side out over a weighted container such as a 15 milliliter scintillation vial using a rubber band, as indicated by the reference numeral 40 of FIG. 1. The container 40 was placed into a 500 milliliter beaker 42 containing gastric fluid. The beaker 42 was placed under the scale portion of the modified tensiometer as illustrated in FIG. 1.

A separate portion of excised stomach tissue was separated into two layers of smooth muscle; i.e., the external longitudinal layer and the internal circular layer. A piece of the internal circular layer was placed mucosal side out over a No. 2 rubber stopper, and the tissue was secured to the rubber stopper using an aluminum vial cap having a uniform-sized opening of about 0.78 square centimeters. The aluminum vial cap is available from Wheaton Company of Millville, N.J. A holding means in the form of screw eye was inserted into the opposite end of the rubber stopper from that to which the tissue was secured. The rubber stopper containing the holding means and affixed tissue was placed in an aerated, chilled normal saline solution until used.

One hundred microliters of gastric fluid was added to 4 milligram samples of each polymer whose bioadhesion was to be measured. One hour after that addition, the swollen polymer was carefully spread over the tissue on the rubber stopper. Any excess of fluid was removed from the polymer by blotting with a tissue paper. The rubber stopper with holding means, tissue and polymer 44 was suspended from the scale so that it rested in the beaker of gastric fluid. When the polymer layer was at a depth equal to that of the tissue already in the container on vial 40, the scale was adjusted to zero using appropriate weights. The rubber stopper with holding means, tissue and polymer 44 was then suspended over the tissue on the weighted container 40, and that container 40 was elevated to contact the polymer using the elevation means 46. Care was taken to assure that the tissue on the container 40 touched only the polymer.

The beaker was then slowly raised until the tissues came into contact, the contact being initiated by the weight of the rubber stopper (1.8 grams). After one minute, the weight was removed, and the force required to separate the polymer from the tissue was measured. The force exerted to separate the layers of stomach tissue was increased at a constant rate of 10 milligrams per second in weight until the tissues separated.

One measurement was carried out within five minutes of contact between the tissue and adhesive of rubber stopper 44 and the tissue of the vial 40. Excised stomach tissue was affixed to either the vial or rubber stopper within 30 minutes of sacrificing the rabbit and is thereby considered to be freshly excised tissue.

Exemplary results using the above measurement technique are illustrated for four useful bioadhesives in Table 2 hereinafter. The bioadhesives were prepared as described in Example 1 with the exception that 0.3 weight percent of cross-linking agent was utilized. After the preparation, the bioadhesives were sieved and dry particles having a 30/40 mesh size (U.S. Standard Sieve Series) were used for these measurements.

TABLE 2

| | Bioadhesion Measurements | | |
|---|---|---|---|
| Polymer[1] | Weight to Separate Tissues[2] | Force to Separate Tissues[3] | Number of Measurements |
| 1 | 855 ± 55 | 1061 ± 68 | 13 |
| 2 | 864 ± 56 | 1072 ± 68 | 12 |
| 3 | 876 ± 57 | 1086 ± 71 | 13 |
| 4 | 306 ± 45 | 380 ± 56 | 8 |

[1]Polymer 1 = polyacrylic acid cross-linked with 3,4-dihydroxy-1,5-hexadiene; polymer 2 = polyacrylic acid cross-linked with 2, 5-dimethyl-1,5-hexadiene; polymer 3 = polyacrylic acid cross-linked with divinylbenzene; and polymer 4 = polymethacrylic acid cross-linked with divinylbenzene.
[2]Weights are in milligrams ± standard error of the mean (S.E.M.)
[3]Forces are reported in dynes/cm$^2$ ± S.E.M.

Using the above measuring technique, p-HEMA commercially available from Aldrich Chemical Co. of Milwaukee, Wis., required a force of 29 dynes/cm$^2$ to separate the tissues, while AMBERLITE® 200 cationic exchange resin available from Rohm and Haas Co. of Philadelphia, Pa., required almost no force to separate the tissues.

EXAMPLE 3

Bioadhesion as a Function of pH Value

Figure 2:
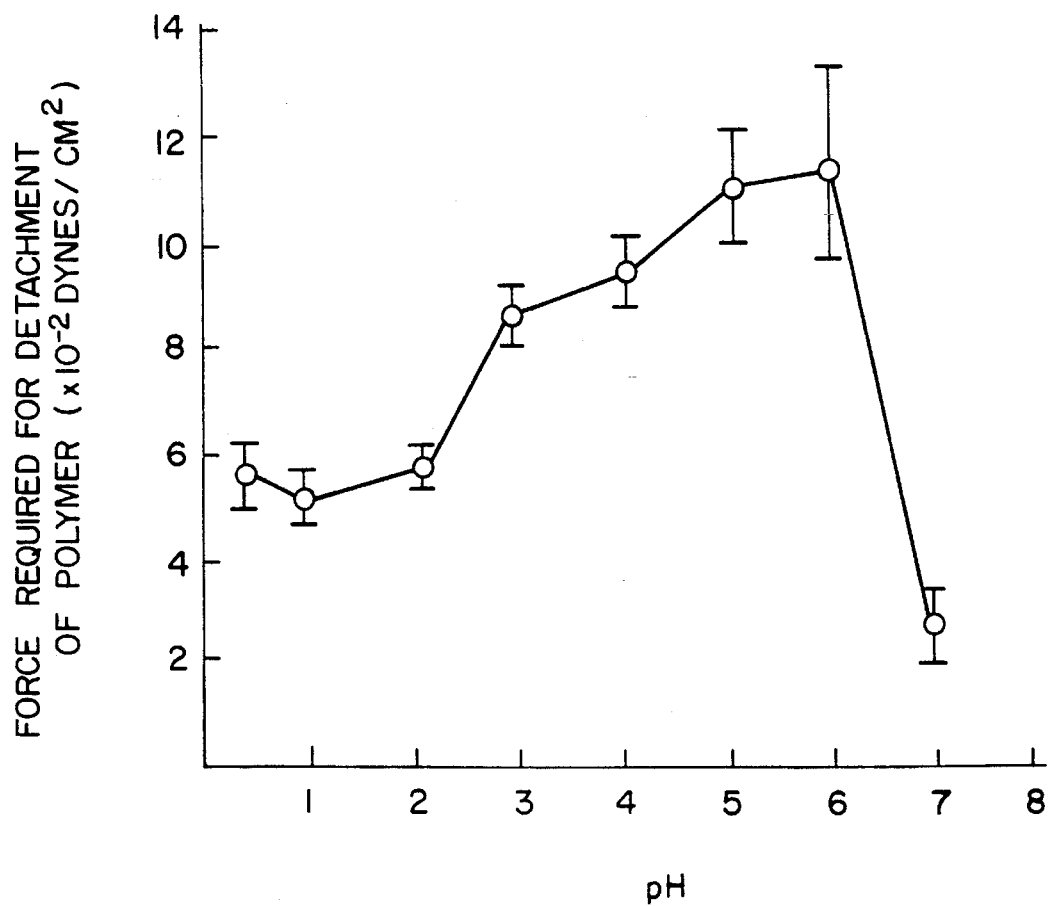
FIG. 2 is a graph illustrating the force (dynes$\times 10^{-2}$/cm$^2$) for detaching a bioadhesive polymer reaction product of acrylic acid copolymerized with 0.3 weight percent 3,4-dihydroxy-1,5-hexadiene having a density of 1.56 grams/cubic centimeter (g/cc) versus pH value.

The force measured to separate a bioadhesive polymer that is the reaction product of the polymerization of acrylic acid with 0.3 weight percent of 3,4-dihydroxy-1,5-hexadiene that had a density of 1.56 g/CC is shown in FIG. 2. As is seen from the Figure, the maximum adhesion was observed at a pH value of about 5 to about 6. That maximum value was more than twice the adhesive force required for the separation at pH values of 0.46, 1.42 or 2.0. As is also seen, adhesion provided by that bioadhesive polymer was substantially reduced at pH value of 7. That reduction was statistically significant in a Student's t-test, p less than 0.01. Bioadhesive forces were measured as discussed previously in Example 2.

EXAMPLE 4

Method of Moisturizing Dry Vagina

A moisturizing composition containing dry polycarbophil (20 g, B. F. Goodrich EX55) sized to pass through a 400 mesh sieve screen (U.S. Standard Sieve Series) and whose number average longest dimensions are less than about 20 microns, CARBOPOL® 934 (10 g; B.F. Goodrich), a hydrogenated palm oil glyceride dispersant [10 g, MYVEROL 18–04K (Eastman)], heavy mineral oil (U.S.P. heavy; 50 ml, Purepac), glycerin U.S.P. (100 ml, Purepac), methyl paraben (1.0 g) and distilled, deionized water up to 1000 g was prepared by admixing with agitration as an emulsion. The pH value was adjusted to pH 2.4 with a solution of sodium citrate in HCl.

About 4 g of the above composition are placed into a plunger-type applicator. The applicator and its contents are placed into the vagina of a post-menopausal woman presenting with dry vagina and vaginitis, and the plunger is depressed to expel the composition into the subject's vaginal cavity to thereby contact the vaginal mucosa. The composition so applied moisturizes the mucosa and also provides lubrication for sexual intercourse.

EXAMPLE 5

Comparative Viscosity Study

Three aqueous vaginal moisturizing compositions substantially identical to the composition of Example 4 were prepared, but in which the amounts of polycarbophil as bioadhesive moisturizing polymer was varied and CARBOPOL® 934 as consistency-enhancing agent was held constant, with more or less water being used to complete the composition.

All three compositions contained 1 weight percent CARBOPOL® 934. Composition 1 contained 1 weight percent of polycarbophil. Composition 2, like that of Example 4, contained 2 weight percent polycarbophil, whereas Composition 3 contained 3 weight percent polycarbophil. Composition 1 was deemed too thin for use although it had a creamy consistency. Composition 3 was too thick for dispensing. Composition 2 had an appropriate viscosity for dispensing with a plunger-type apparatus and exhibited a good feel when rubbed on the skin.

EXAMPLE 6

Viscosity Measurements

A moisturizing composition of the present invention is viscous, preferably having a gel-like consistency that is somewhat thicker or more viscous than mayonnaise. Such a composition exhibits non-Newtonian flow characteristics that can be described as thixotropic; i.e., the flow is characterized by 1) a yield point, 2) pseudoplastic behavior, 3) a reduction in viscosity on continued shearing, visible over a finite time, and 4) a tendency to rebuild viscosity and/or yield point on standing.

Because of the non-Newtonian character of a contemplated moisturizing composition, viscosity measurements are made in a viscometer that is especially designed for such fluids. Viscosity values are therefore reported at a noted temperature and shear rate, using a particular viscosimeter.

The viscometer utilized for the viscosity measurements discussed herein is a commercially available Haake ROTOVISCO Model RV-12, available from Haake, Inc., 244 Saddle Brook Road, Saddle Brook, N.J. 07662. The machine utilized an SV cup and an SVII rotor for determining viscosity in centipoises (cps) at shear rates of 1–8 revolutions per minute (rpm) and at a temperature of 25 degrees C.

Two exemplary moisturizing compositions prepared as discussed in Example 4 were made separately, by different persons. The viscosities of both compositions were separately measured at shearing rates of 1, 2, 4 and 8 rpm, and then compared.

Figure 3:
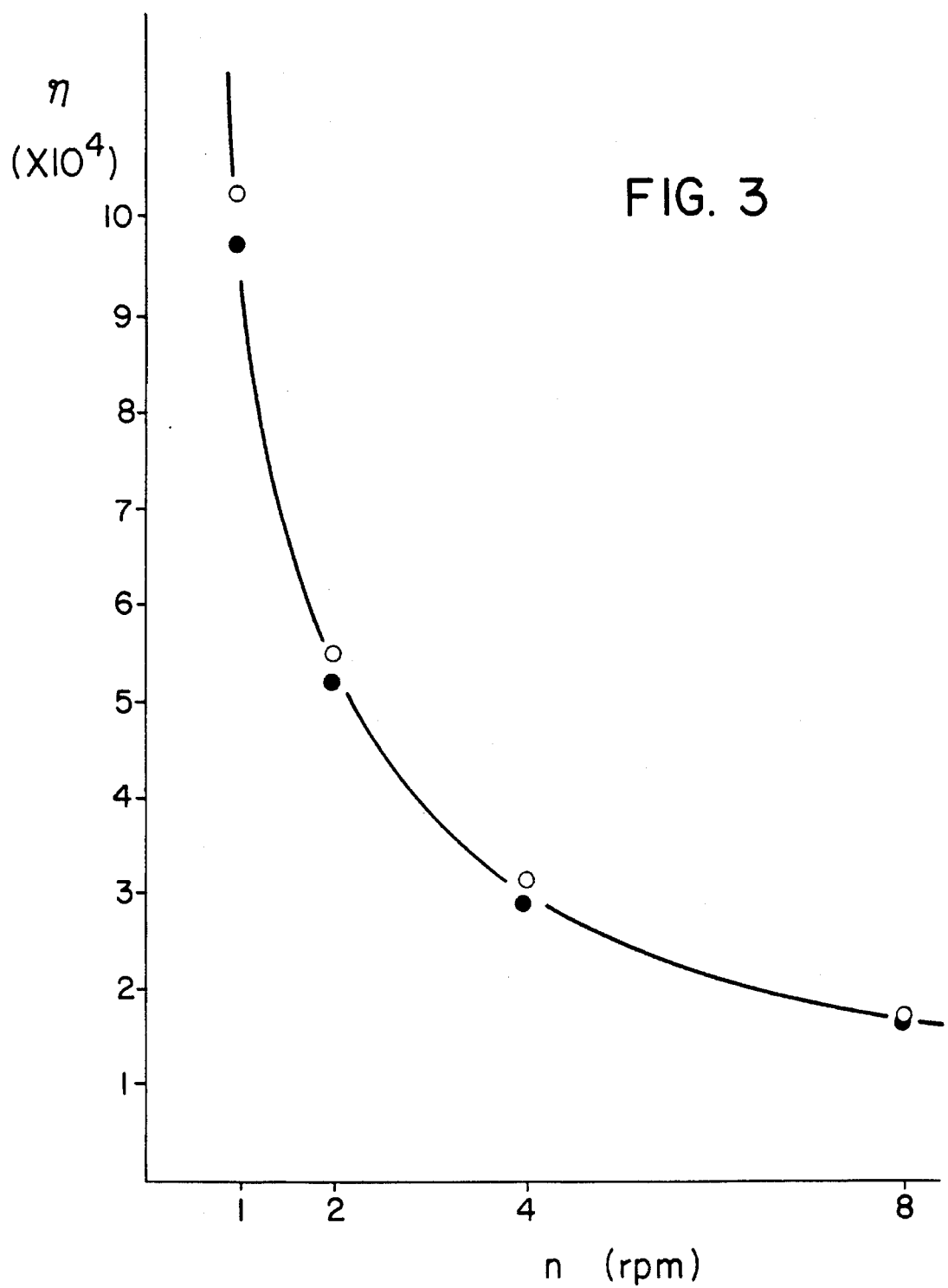
FIG. 3 is a graph of viscosity, $\eta$, in cps from 10,000–100,000, shown for convenience as 1–10 $\times 10^4$, versus shear rate, n, in rpm for two separately made moisturizing compositions prepared as described in Example 4. The results were obtained using a Haake ROTOVISCO Model RV-12 viscometer as discussed in Example 6, and data for one composition are shown in closed circles, whereas data for the other are shown in open circles.

The results of this comparison are illustrated in FIG. 3 in which viscosity, η, in cps X10$^4$ is plotted against the shearing rate, n, in rpm. Open and closed circles are utilized to show datum points for one or the other of the compositions.

The foregoing is intended as illustrative of the present invention but not limiting. Numerous variations and modifications may be effected without departing from the true spirit and scope of the novel concepts of the invention.

I claim:

1. A method of moisturizing mammalian vaginal mucous membrane comprising:

(A) contacting mammalian vaginal mucous membrane with an aqueous composition in an amount effective to moisturize vaginal mucosal cells, said aqueous composition, being essentially free of a treating agent, and comprising:

(1) water, (2) a moisturizing amount of a bioadhesive, moisturizing, substantially non-esterified polymer in a free acid form, said bioadhesive polymer consisting essentially of particles of a water-swellable, but water-insoluble, cross-linked carboxyl-functional polymer that consists essentially of (a) a plurality of repeating units of which at least about 80 percent contain at least one carboxyl functionality, and b) about 0.05 to about 1.5 weight percent of a crosslinking agent free of polyalkenyl polyether; and (3) a thickening-smoothing amount of a consistency-enhancing agent, said consistency-enhancing agent being a water-dispersible, non-ionic or anionic polymer; and (B) maintaining said contact for a time period sufficient to moisturize said contacted vaginal mucous membrane.

2. The method according to claim 1 wherein said bioadhesive polymer particles are sized to pass through a 400 mesh size sieve, U.S. Standard Sieve Series, when dry.

3. The method according to claim 2 wherein said bioadhesive polymer particles have a number average longest dimension of about 2 to about 5 microns.

4. The method according to claim 1 wherein at least about 90 percent of said repeating units contain at least one carboxyl functionality.

5. The method according to claim 1 wherein said consistency-enhancing agent is an anionic polymer having a plurality of carboxyl groups.

6. The method according to claim 1 wherein said consistency-enhancing agent is present at about 0.25 to about 10 weight percent of said composition.

7. A method of moisturizing mammalian vaginal mucous membrane comprising:

(A) contacting mammalian vaginal mucous membrane with an aqueous composition in an amount effective to moisturize vaginal mucosal cells, said aqueous composition, being essentially free of treating agent and comprising:

(1) water;

(2) a moisturizing amount of a bioadhesive moisturizing substantially non-esterified polymer in a free acid form, said bioadhesive polymer consisting essentially of particles of a water-swellable, but water-insoluble, cross-linked carboxyl-functional polymer present at about 0.25 to about 5 weight percent of said composition, said polymer particles sized to pass through a 400 mesh size sieve, U.S. Standard Sieve Series and consisting essentially of (a) a plurality of repeating units of which at least about 80 percent contain at least one carboxyl functionality, and (b) about 0.05 to about 1.5 weight percent of a crosslinking agent free of polyalkenyl polyether; and (3) a consistency-enhancing agent, said consistency-enhancing agent being a water-dispersible non-ionic or anionic polymer having a plurality of carboxyl groups that is present in an amount of about 0.5 to about 5 weight percent of said composition; and (B) maintaining said contact for a time period sufficient to moisturize said mucous membrane.

8. The method according to claim 7 wherein said composition has a gel-like consistency.

9. The method according to claim 8 wherein the vaginal mucosa are contacted with about 1 to about 5 grams of said composition that contains about 0.25 to about 3 weight percent of said bioadhesive polymer.

10. The method according to claim 8 wherein said consistency-enhancing agent is a cross-linked anionic polymer.

11. The method according to claim 8 wherein said consistency-enhancing agent is polyacrylic acid cross-linked with the polyallyl sucrose containing an average of at least three allyl groups per molecule.

12. The method according to claim 8 wherein said composition further includes one or more pharmaceutically or cosmetically acceptable adjuvants selected from the group consisting of a preservative, emollient, lubricating oil, emulsifying agent, humectant, coloring agent and odorant.

13. A vaginal moisturizing composition consisting essentially of:

(A) water;

(B) an amount sufficient to moisturize vaginal tissue of a substantially non-esterified bioadhesive in a free acid form moisturizing polymer, said bioadhesive moisturizing polymer consisting essentially of particles of a water-swellable, but water-insoluble cross-linked carboxyl-functional polymer that consists essentially of (a) a plurality of repeating units of which at least about 80 percent contain at least one carboxyl functionality, and (b) about 0.05 to about 1.5 weight percent of a cross-linking agent that is substantially free from polyalkenyl polyether; and (C) a thickening-smoothing amount of a consistency-enhancing agent, said consistency-enhancing agent being a water-dispersible non-ionic or anionic polymer.

14. The composition according to claim 13 wherein said bioadhesive polymer particles are sized to pass through a 400 mesh size sieve, U.S. Standard Sieve Series, when dry.

15. The composition according to claim 14 wherein said bioadhesive polymer particles have a number average longest dimension of about 2 to about 5 microns.

16. The composition according to claim 13 wherein at least about 90 percent of said repeating units contain at least one carboxyl functionality.

17. The composition according to claim 13 wherein said consistency-enhancing agent is an anionic polymer having a plurality of carboxyl groups.

18. The composition according to claim 13 wherein said consistency-enhancing agent is present at about 0.25 to about 10 weight percent of said composition.

19. A vaginal moisturizing composition consisting essentially of:

(A) water;

(B) an amount sufficient to moisturize a vagina of a substantially non-esterified bioadhesive in a free acid form moisturizing polymer, said bioadhesive moisturizing polymer consisting essentially of particles of a water-swellable, but water-insoluble, cross-linked carboxyl-functional polymer consisting essentially of (a) a plurality of repeating units of which at least about 80 percent contain at least one carboxyl functionality, and (b) about 0.05 to about 1.5 weight percent of a cross-linking agent that is substantially free from polyalkenyl ether;

(C) a thickening-smoothing amount of consistency-enhancing agent, said consistency-enhancing agent being a water-dispersible non-ionic or anionic polymer; and (D) an adjuvant selected from the group consisting of a preservative, emollient, lubricant, emulsifying agent, humectant, coloring agent, odorant and perfume.

20. The composition according to claim 19 wherein said composition has a gel-like consistency.

21. The composition according to claim 20 wherein the vaginal mucosa are contacted with about 1 to about 5 grams of said composition that contains about 0.25 to about 3 weight percent of said bioadhesive polymer.

22. The composition according to claim 20 wherein said consistency-enhancing agent is polyacrylic acid cross-linked with polyallyl sucrose containing an average of at least three allyl groups per molecule.

* * * * *